(12) United States Patent
Deitcher et al.

(10) Patent No.: US 11,531,394 B2
(45) Date of Patent: Dec. 20, 2022

(54) SYSTEMS AND METHODS FOR EMOTIONAL-IMAGING COMPOSER

(71) Applicant: EMOTIONAL IMAGING INC., Montreal (CA)

(72) Inventors: Jordan Deitcher, Montréal (CA); Mitchel Benovoy, Montréal (CA); Johnty Wang, Vancouver (CA)

(73) Assignee: EMOTIONAL IMAGING INC., Montréal (CA)

( * ) Notice: Subject to any disclaimer, the term of this patent is extended or adjusted under 35 U.S.C. 154(b) by 0 days.

(21) Appl. No.: 17/408,209

(22) Filed: Aug. 20, 2021

(65) Prior Publication Data

US 2022/0075450 A1 Mar. 10, 2022

Related U.S. Application Data

(60) Provisional application No. 63/075,949, filed on Sep. 9, 2020.

(51) Int. Cl.
| | |
|---|---|
| *G06F 3/01* | (2006.01) |
| *G06T 11/00* | (2006.01) |
| *G06N 20/00* | (2019.01) |
| *A61B 5/16* | (2006.01) |
| *B25J 11/00* | (2006.01) |

(52) U.S. Cl.
CPC .............. *G06F 3/015* (2013.01); *A61B 5/165* (2013.01); *G06N 20/00* (2019.01); *G06T 11/001* (2013.01); *B25J 11/001* (2013.01); *G05B 2219/36488* (2013.01); *G06F 2203/011* (2013.01); *G06T 2200/24* (2013.01); *G06T 2210/56* (2013.01)

(58) Field of Classification Search
CPC ... G06F 3/015; G06F 2203/011; G06N 20/00; A61B 5/165; G06T 11/001; G06T 2200/24; G06T 2210/56; B25J 11/001; G05B 2219/36488
USPC ....................................................... 345/156
See application file for complete search history.

(56) References Cited

U.S. PATENT DOCUMENTS

| | | | | |
|---|---|---|---|---|
| 9,711,060 | B1 * | 7/2017 | Lusted | A61B 5/02416 |
| 9,874,862 | B2 * | 1/2018 | Lee | A61B 5/6898 |
| 10,825,564 | B1 * | 11/2020 | Zhang | G16H 15/00 |
| 2016/0364895 | A1 * | 12/2016 | Santossio | G06Q 50/01 |
| 2018/0275747 | A1 * | 9/2018 | Campbell | G09G 3/2096 |
| 2019/0110103 | A1 * | 4/2019 | el Kaliouby | G08G 1/096716 |
| 2019/0268660 | A1 * | 8/2019 | el Kaliouby | A61B 5/165 |
| 2020/0202445 | A1 * | 6/2020 | Zang | G06F 3/015 |
| 2021/0001862 | A1 * | 1/2021 | Senechal | G06T 3/0006 |
| 2021/0307664 | A1 * | 10/2021 | Bey | A61B 5/681 |
| 2022/0036481 | A1 * | 2/2022 | Curtis | H04L 51/10 |

* cited by examiner

*Primary Examiner* — Tom V Sheng
(74) *Attorney, Agent, or Firm* — Greenberg Traurig LLP

(57) ABSTRACT

Systems and methods for Emotional-Imaging Composer are disclosed. The method may include recording a real-time biosignal from a plurality of biosignal sensors. The method may further include determining an emotion that is associated with the real-time biosignal. The method may further include outputting a display feature corresponding to the emotion, wherein the display feature is a lighting effect on a graphical user interface.

17 Claims, 7 Drawing Sheets

SYSTEMS AND METHODS FOR EMOTIONAL-IMAGING COMPOSER

CROSS-REFERENCE TO RELATED APPLICATION

This application claims priority to U.S. provisional application No. 63/075,949, filed on Sep. 9, 2020, which application is hereby incorporated by reference in its entirety.

TECHNICAL FIELD

The instant disclosure generally relates to systems and methods for Emotional-Imaging Composer.

BACKGROUND

A human body generates numerous signals, such as brainwaves and the electrical signals that control a heartbeat. Systems currently exist to measure and monitor such biosignals generated by a body of a person.

SUMMARY

Systems and methods for an Emotional-Imaging Composer are disclosed. The method may include recording a real-time biosignal from a plurality of biosignal sensors. The method may further include determining an emotion that is associated with the real-time biosignal. The method may further include outputting a display feature corresponding to the emotion, wherein the display feature is a lighting effect on a graphical user interface.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Measured biosignals, such as brainwaves measured by electroencephalograms (EEG), heart signals measured by electrocardiogram (ECG), and the like, can be converted into digital form for purposes ranging from psychological therapies to gaining Embodiments of this disclosure include systems and methods for composing emotional images from biosignals. For example, embodiments may leverage the use of one or more (e.g., multiple) machine learning models to extract features from biometric sensor data in real time (or near real time) to generate a predicted emotion and a corresponding scene that represents the predicted emotion.

Figure 1:
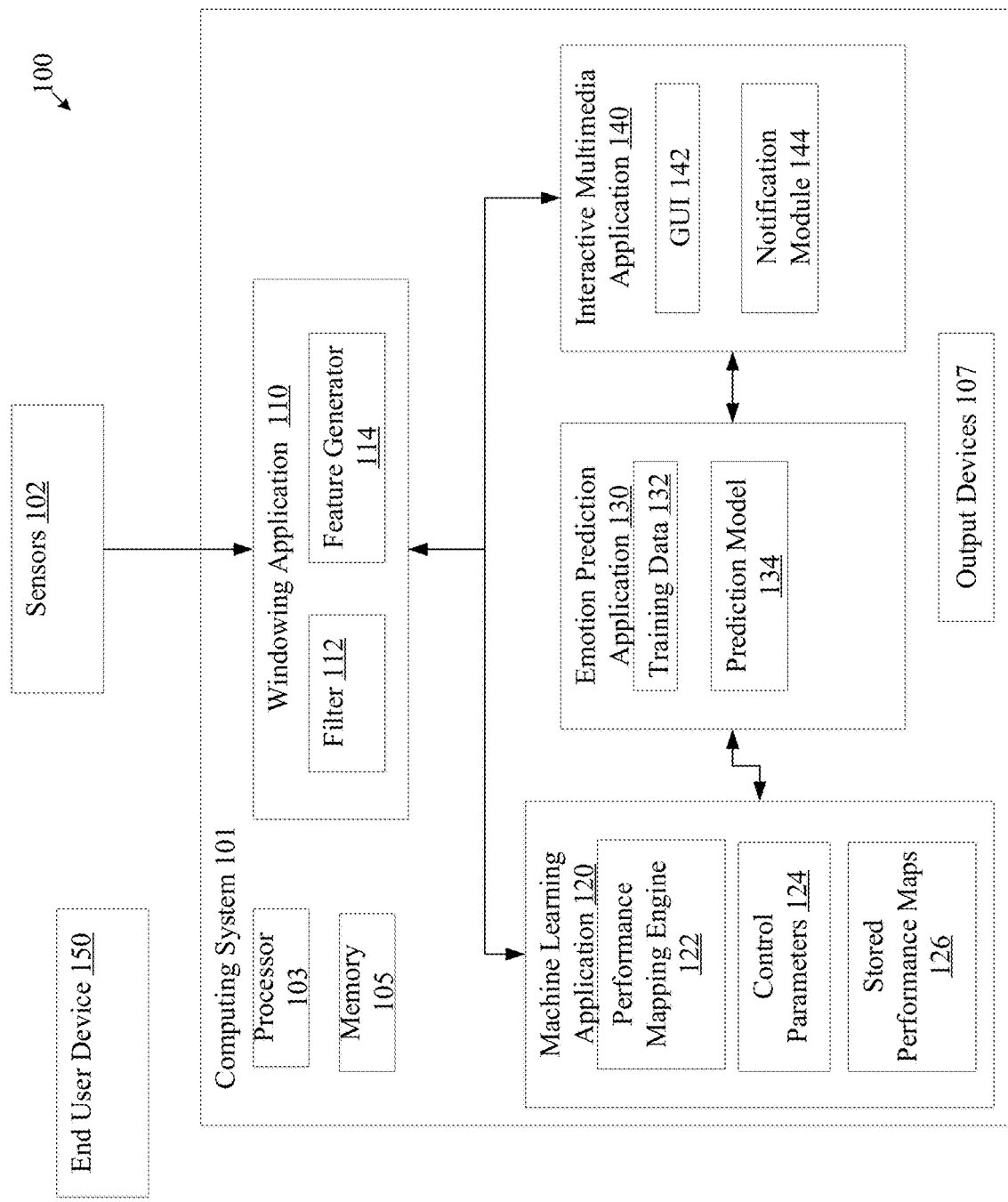
FIG. 1 depicts an example of a system for an Emotional-Imaging Composer, according to certain embodiments of the present disclosure.

Referring now to the figures, FIG. 1 depicts a system 100 (referred to herein as an "Emotional-Imaging Composer Composer") for Emotional-Imaging Composer, according to certain embodiments of the present disclosure. The Emotional-Imaging Composer 100 may include one or more sensors 102 (e.g., a plurality of sensors 102), a computing system 101 and one or more output devices 107. The computing system 101 may include a processor 103 and a non-transitory, computer-readable memory 105 storing instructions. The processor 103 may be configured to execute the instructions to perform one or more steps, algorithms, operations, methods, processes, etc. of this disclosure. The computing system 101 may include one or more functional applications that may be embodied in hardware and/or software (e.g., in instructions in the memory 105), including a windowing application 110, a machine learning application 120, an emotion prediction application 130, and an interactive multimedia application 140.

The system 100 may operate in one or more modes. For example, the system 100 may operate in a training mode in which the system 100 trains the emotion prediction application 130, a composing mode in which the system 100 provides the user with an opportunity to record emotions and biosignal data, and/or a performing mode in which the system 100 provides real-time emotion prediction (i.e., determination of the user's present emotional state) and outputs a visual or lighting feature corresponding to the determined emotion. As one of skill in the art will appreciate, while FIG. 1 depicts each of these applications 110, 120, 130, 140 as separate applications, one or more of these applications 110, 120, 130, 140 may be combined as desired without departing from the teachings of the present disclosure.

The system 100 may be used by a user to, for example, enhance a dramatic performance, with the system 100 determining the emotion being performed by the user and altering an aspect of the user's environment, such as a display or lighting, accordingly. One way that this can be done is through the mapping of these input signals to control the parameters of algorithmic or generative synthesis systems."

In one example, sensors 102 may include biometric sensors such as an electroencephalogram (EEG) sensor, electromyograph (EMG) sensor, blood volume pulse (BVP) sensor, galvanic skin response (GSR) sensor, one or more skin temperature monitors, and the like.

The windowing application 110 may be configured to receive a stream of data from, or a set of previously-recorded data respective of, the sensors 102. In some embodiments, the windowing application may capture (e.g., define for analysis) a dynamic temporal window of data from the sensors 102. For instance, the windowing application 110 may define an initial 3-second window for the data received from sensors 102. The windowing application 110 may adjust the length of the window based on an emotion, a quality of sensor data, or a rate of change of the data from sensors 102. Concurrent windows of different sizes may also be used in parallel for the simultaneous detection of features that may span different time scales.

The windowing application 110 may include filter 112 and feature generator 114. The filter 112 may perform filtering operations on received sensor data. In one example, the filter 112 may normalize the set of sensor data to a baseline range of sensor data values. In one aspect, the filter 112 may normalize the set of sensor data by computing a mean value for each type of sensor, establishing a minimum normalized value and a maximum normalized value, and transform the set of sensor data into the range between the minimum normalized value and maximum normalized value. In one example, the filter may normalize previously recorded data or also may perform normalization in real-time with predetermined values that are used to normalize newly received data. The filter 112 may also identify or remove sensor data that is erroneous or otherwise unsuitable for use in the emotion prediction model due to sensor failure, sensor measurement error, or ambient environment impacts. For instance, the filter 112 may determine that a data value of the sensor data exceeds a sensor threshold (e.g., a value outside of an upper or lower bound) for actual data measured for a user.

The feature generator 114 may include a deep learning model to extract features from the filtered sensor data. An example of a feature may be a raw value of the biosignal, a change in value of a biosignal, or changes in the raw values (or change between values) for a combination of values of biosignals, which indicate an emotion. The deep learning model may be trained to recognize a predetermined set of features in the filtered sensor data. The deep learning model may be trained using training data that includes various features that indicate predetermined emotions. In other examples, the deep learning model may determine sets of features that may be extracted based on feedback from the emotion prediction application 130. In these examples, the deep learning model may learn new features that improve accuracy in predicting emotion. In some embodiments, the feature generator 114 may determine a subset of sensor data to be input to the emotion prediction application for generating an emotion prediction. The feature generator 114 may receive feedback (e.g., user feedback or a machine learning feedback such a loss factor) from the emotion prediction application 130. In response to receiving the feedback from the emotion prediction application 130, the feature generator 114 may adjust the subset of sensor data based on the feedback. The feature generator 114 may also retrain the deep learning model to an updated set of features to extract from the filtered sensor data to improve the accuracy of the prediction of a particular emotion. In some aspects, the feature generator 114 may also be configured to receive feedback from a user through the emotion prediction application 130 during a training phase. During the training phase, the emotion prediction application 130 may prompt a user to demonstrate a particular emotion and receive feedback from the user on the correlation of the biosignal values recording during the training to the prompted emotion.

The feature generator 114 may receive data from the sensors 102 in native sensor format and extract feature data in vector, matrix, or other format. The feature generator 114 may further determine, based at least in part on the feedback from the emotion prediction application 130, a similarity of two or more features to one another such that the similarity indicates that those features provide similar input to the emotion prediction application 130.

Machine learning application 120 may include a performance mapping engine 122 and a set of control parameters 124. The machine learning application 120 may receive output from windowing application 110 (e.g., a set of sensor data within a time window defined by the windowing application 110). The machine learning application 120 may determine respective values for one or more control parameters 124. In some embodiments, the control parameters 124 may include one or more particle behavior values as described with regard to FIG. 4B. Examples of control parameters 124 may include a start speed, lifetime, velocity, number of particles, noise, gravity, size, color, and the like.

The performance mapping engine 122 may be or may include a machine learning model that captures performance parameters of the emotion prediction application 130, the windowing application 110, and the prediction model 134. The performance parameters may be used as weights of the emotion prediction application 130 and may be based on feedback from a user based on a predicted emotion and an intended emotion of the user. For instance, the emotion prediction application 130 may present various prediction emotions to the user and may receive an evaluation from the user of accuracy (e.g., predicted emotion is "very angry," and user provides feedback that the emotion experienced or intended was "slightly angry") The emotion prediction application may use the performance parameters to adjust weights such as using the user feedback during a re-training of a machine learning model of the machine learning application 120 or during a retraining process of such a model.

Emotion prediction application 130 may include training data 132 and a prediction model 134. The emotion prediction application 130 may train the prediction model 134 using training data 132. In one example, the prediction model 134, which may be a neural network or similar type of machine learning model, may be trained with training data including one or more training biosignals with a corresponding ground truth emotion. In some aspects, the prediction model may be trained in a supervised, semi-supervised, or unsupervised training environment. Once trained, the prediction model 134 may receive one or more real-time or recorded biosignals as input and may output a determined emotion based on the received biosignals. The emotion prediction application 130 may further be configured to output a predicted (i.e., determined) emotion based on one or more outputs from the prediction model 134. In one embodiment, the emotion prediction application 130 may output a set of particle behaviors to the interactive multimedia application 140. In one example, a set of particle behaviors may be defined by actions or attributes of individual particles in a particle cloud such as described with regard to FIGS. 4A-B. In other embodiments, the emotion prediction application 130 may output a notification or alert including the predicted emotion. For instance, the emotion prediction application 130 may output a notification (e.g., a visual alert, an audible alert, and/or a haptic alert) to an end user device 150 and provide one or more tips to the user to modify or decrease the intensity of the predicted emotion.

In a non-limiting example, the emotion prediction application 130 may predict an anger emotion with a magnitude that is greater than a threshold. The magnitude of the anger emotion may be determined based on a distance from the set point representative of the user's emotional state to an average set point representative of anger for a plurality of users similar to the user. The emotion prediction application 130 may notify the user that the emotion prediction application has projected them in a high anger emotion state. The emotion prediction application 130 may provide the user with contact information for resources such as anger management, an urgent care provider, or counseling service based on a current location of the user. In some embodiments, the emotion prediction application may determine that a projected trajectory of the predicted emotion places the user in a high anger emotion state. The emotion prediction application may determine the trajectory based on a rate of change, direction, or acceleration of predicted emotion towards a set point corresponding to the anger emotion state.

Interactive multimedia application 140 may include a graphical user interface (GUI) output portion 142 and a notification application 144. The GUI output portion 142 may be configured to generate and/or output a GUI to the end user device 150, wearable device, or the like. The GUI 142 may be configured to present information to a user and receive input from the user based on the predicted emotion, or the emotion state of the user. The notification application 144 may be communicatively coupled to the emotion prediction application 130. The notification application 144 may alert the user using audio, visual, or haptic cues that a particular emotion is predicted. As described with regard to the emotion prediction application 130, the notification application 144 may communicate with the user to indicate that an exceedingly strong emotion response is projected based on the trajectory, rate of change, or acceleration of the predicted emotion. The notification application 144 may also transmit the notification to a medical provider, emergency contact, or the like based on the profile of the user and with the user's consent.

The output device 107 may be or may include a display, projector, projection mapping system, virtual reality headsets, audio synthesis system, headphones, speaker, haptic system, and/or any other device that may produce a visual, audible, tactile, or other output evocative of a determined emotion for inclusion of a performance of that emotion.

Figure 2:
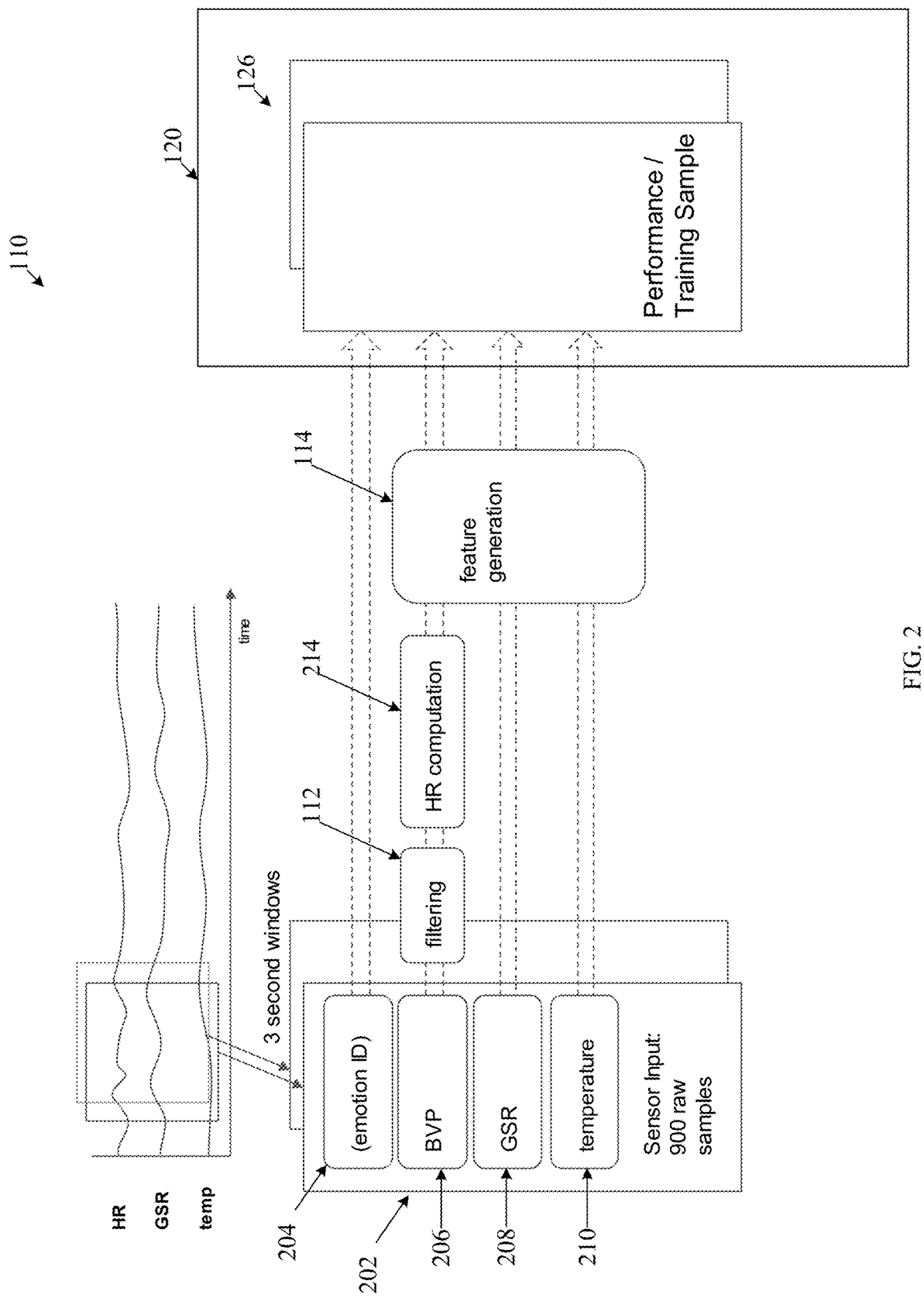
FIG. 2 depicts an example of a process flow for windowing and filtering for the Emotional-Imaging Composer, according to certain embodiments of the present disclosure.

FIG. 2 depicts an example functional diagram of the windowing application 110 for Emotional-Imaging Composer, according to certain embodiments of the present disclosure. The windowing application 110 may include one or more sets of sensor data 202, filter 112, heart rate computation engine 214, feature generator 114, and machine learning application 120. The sensor data 202 may be capture from a plurality of sensors, such as sensors 102. The windowing application 110 may receive the set of sensor data 202 from the sensors as described with regard to FIG. 1. The windowing application 110 may output sensor data (e.g., filtered and windowed sensor data) to the machine learning application 120.

A set of sensor data 202 may include an emotion identifier (emotion ID) 204, a blood volume pulse (BVP) 206, a galvanic skin response (GSR) 208, and a temperature 210. The data points within a single sensor data set may have been collected during a single time window, and the windowing application 110 therefore may store a plurality of sensor data sets, each corresponding to a respective time window, in some embodiments. The windowing application 110 may assign an emotion ID 204 to each set of sensor data 202 as a unique identifier for each set of sensor data 202. In one example, the emotion ID 204 may be unique to the set of sensor data as to the specific analysis window such that no two sets of sensor data have a common emotion ID 204. Additionally, the emotion ID 204 may be used to trace a real-time predicted emotion to a particular set of sensor data and a particular time window for additional analysis as desired. A set of sensor data 202 may be or may include native data from each type of sensor. The windowing application 110 may dynamically assign a window length to each set of sensor data 202, with each set of sensor data containing one window length of data from each sensor (e.g., a set of data includes one time interval of each sensor). For example, the windowing application 110 may set an initial length such as 3 seconds based on a predetermined or default time window. In this example, the set of sensor data 202 may include 3 seconds of sensor measurements from each sensor. The windowing application 110 may also adjust the length of the window dynamically during the training, composing, or performing mode. For instance, following the initial window, the windowing application 110 may increase the window length (i.e., longer window) during a low-intensity or steady-state predicted emotion such as when a user may be inactive, sleeping, etc. The windowing application 110 may decrease the window length based on movement of the predicted emotion or indications from the sensor data 202 that the user is alert and active.

The windowing application 110 may process the set of sensor data 202 using filter 112. The filter 112 may apply multiple types of filtering based on aspects of the set of sensor data 202 such as signal to noise ratio, a magnitude of the signal, or a comparison of each of the received signal from a respective sensor with a signal threshold. HR computation 214 may involve computing or measuring a heart-rate of the user based on one or more values of sensor data 202.

Figure 3:
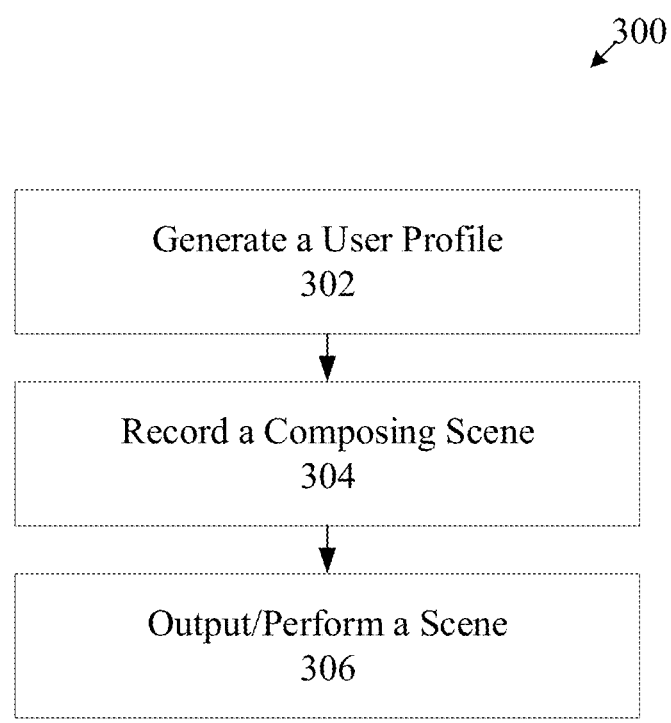
FIG. 3 depicts an example of a process flow of the Emotional-Imaging Composer, according to certain embodiments of the present disclosure.

FIG. 3 depicts an example of a process flow 300 for Emotional-Imaging Composer, according to certain embodiments of the present disclosure. One or more portions of the method 300 may be performed by an Emotional-Imaging Composer (e.g., the emotion prediction module 130), in some embodiments.

At block 302, the process 300 involves generating a user profile. For example, the Emotional-Imaging Composer may have one or more setup modes to generate a user profile.

Figure 4A:
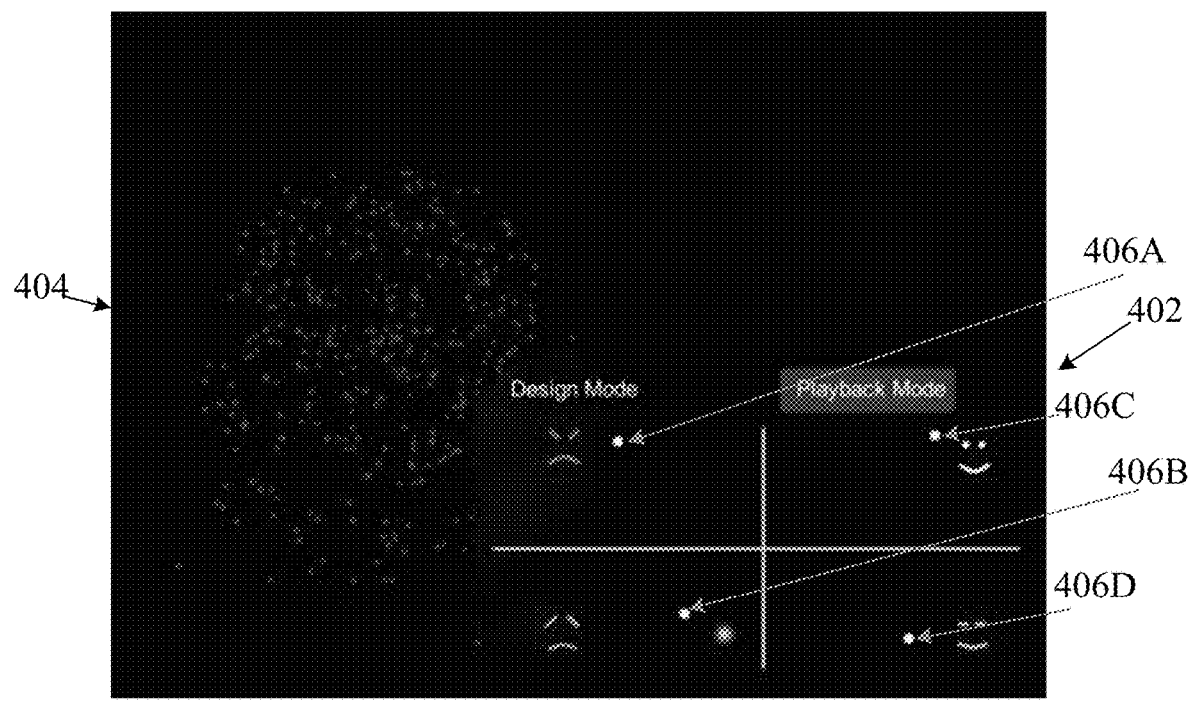
FIG. 4A depicts an example of a graphical user interface (GUI) for generating set points and particle behavior, according to certain embodiments of the present disclosure.
Figure 4B:
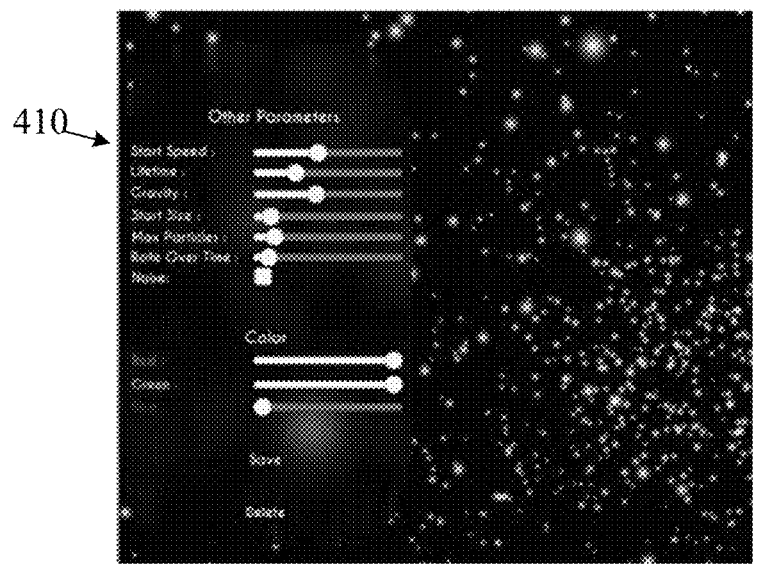
FIG. 4B depicts an example of a GUI for adjusting particle behavior control for the Emotional-Imaging Composer, according to embodiments of the present disclosure.

In one example, the Emotional-Imaging Composer can receive user input via a graphical user interface (GUI), such as the GUI depicted in FIGS. 4A-B. While not depicted in FIGS. 4A-B, the Emotional-Imaging Composer may be configured to interact with multiple users. The Emotional-Imaging Composer may allow a current user to select a profile from a plurality of users profiles. Additional details regarding generating a user profile are described with regard to FIG. 5.

Figure 5:
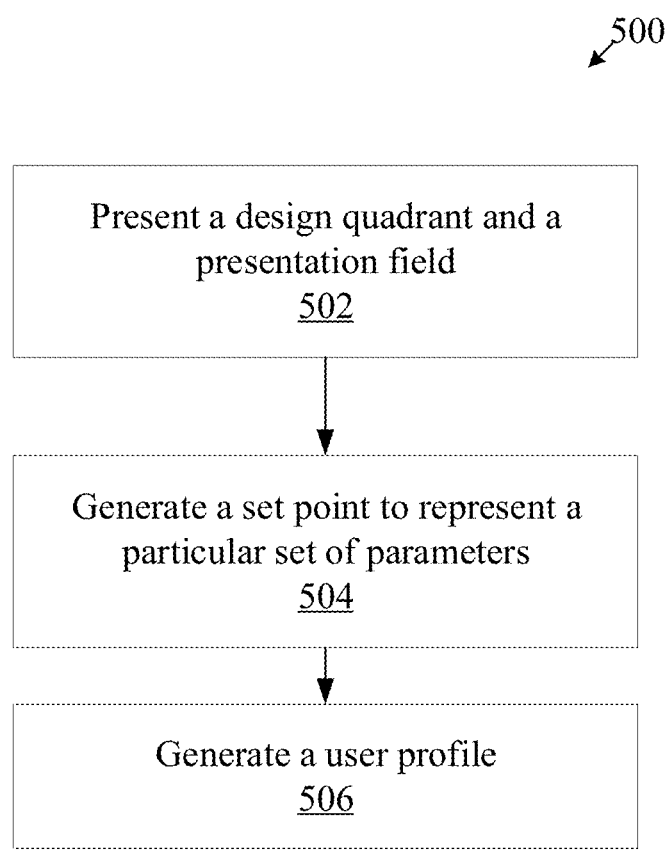
FIG. 5 depicts an example of a process flow of generating a profile for the Emotional-Imaging Composer, according to certain embodiments of the present disclosure.

FIG. 5 is a flow chart illustrating an example method 500 for generating a user profile. One or more portions of the method 500 may be performed by the emotion prediction module 130, in some embodiments.

Referring to FIGS. 4A, 4B, and 5, the method 500 may include, at block 502, presenting a design quadrant 402 and a presentation field 404. The design quadrant may have one or more set points 406A-D, "set points 406." The set points 406 may be user configurable and represent a threshold of an emotion. Block 502 may include the emotion prediction module generating the design quadrant and presentation field and transmitting the design quadrant and presentation field to an end user device, in some embodiments. In other embodiments (e.g., an end user device implementation of the emotion prediction module), block 502 may include the emotion prediction module generating and displaying the design quadrant and presentation field for the user.

The method 500 may further include, at block 504, generating a set point 406A to represent a particular set of parameters that indicate a desired emotion (for example, an "angry" emotion). For example, block 504 may include the Emotional-Imaging Composer presenting a particular behavior in the presentation field 404 based on the generated set point 406A. In some embodiments, block 504 may include generating one or more respective set points for one or more emotions; four such set points 406A, 406B, 406C, 406D for four different emotions are shown in FIG. 4A. The Emotional-Imaging Composer may compute positions of set points 406B-D with a respective particle behavior based on the emotion represented by the applicable set point. The Emotional-Imaging Composer may respond to a selection of set point 406A by presenting a particle behavior that represents the "angry" emotion. The Emotional-Imaging Composer may respond to the selection of set points 406B-D with a respective particle behavior based on the emotion represented by the applicable set point. While FIG. 4A depicts four set points 406, any number of set points may be configured. The Emotional-Imaging Composer may interpolate a position between the set points 406 or between a preset emotion threshold to generate an intermediate particle behavior. The intermediate particle behavior may include an interpolation, or other combination of one or more particle behaviors from set points 406. Additional details relating to the particle behavior is likely best understood with reference to FIG. 4B.

In some embodiments, block 504 may include the Emotional-Imaging Composer automatically generating one or more aspects of the user profile. For example, the Emotional-Imaging Composer may determine a type of a user, such as by demographic data or an assessment record of the user provided by a medical provider. In one example, the Emotional-Imaging Composer may use a threshold distance between set points 406 to assign additional set points relative to set point 406A. The Emotional-Imaging Composer may also use other distances or relationships between each set point to determine the positions of set points 406.

Additionally or alternatively, block 504 may include generating one or more set points based on a classification of the user. The Emotional-Imaging Composer may generate a classification based on user demographic data, medical history data, a behavior profile of the user, or the like. The Emotional-Imaging Composer may assign the user to a pre-determined cluster of profiles based on the similarity of the user's data to the data of the users associated with the clustered profiles. Clusters may have been computed based on a relationship of set points among a plurality of users. For example, the user may be clustered based on a minimization of the aggregate distance between the set points of the user and average set points of a plurality of users.

As one of skill in the art will appreciate, these automations may be combined with one or more inputs from a user via the GUI and further can be configured to augment, in whole or in part, the generation of a user profile. Accordingly, the method 500 may further include, at block 506, receiving user feedback on the generated set points. For example, the user may shift set points inward or outward, upward or downward to set the baseline location of an emotion for that user. The Emotional-Imaging Composer may also be configured to adjust the set points 406 based on the emotion prediction model, or a medical provider, in some embodiments. Following block 506, a user profile that includes set points specific to the user for one or more emotions may be stored. The user profile may further include the user's preferences for the particle or other output behavior associated with each of the one or more emotions.

Returning to FIG. 3 at block 304, the process 300 involves configuring a composing scene. Additional details regarding generating a user profile are described with regard to FIG. 6.

Figure 6:
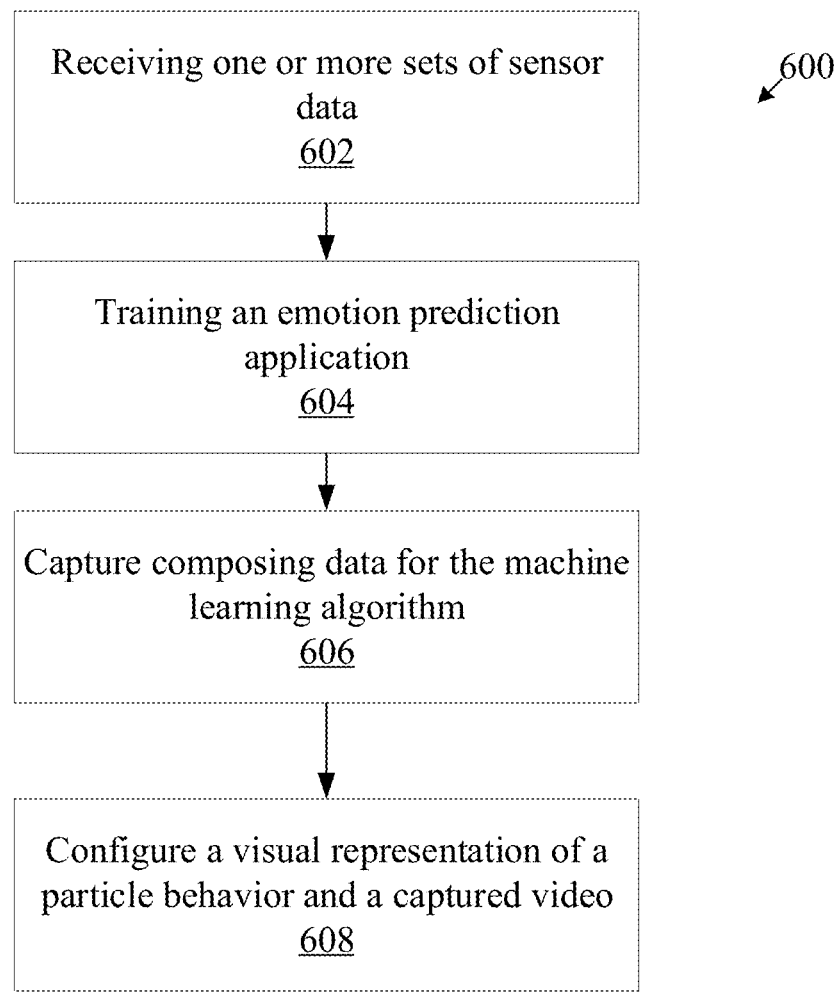
FIG. 6 depicts an example of a process flow of the Emotional-Imaging Composer, according to certain embodiments of the present disclosure.

FIG. 6 is a flow chart illustrating an example method of configuring a composing scene. One or more portions of the method 600 may be performed by the emotion prediction module 130, in some embodiments.

The method 600 may include, at block 602, receiving one or more sets of sensor data from sensors, as described with regard to FIGS. 1-2, for one or more users performing emotions and storing the data in training data.

The method 600 may further include, at block 604, training an emotion prediction application (e.g., one or more machine learning models thereof) using the training data. For instance, the Emotional-Imaging Composer may be trained with supervised, semi-supervised, or unsupervised learning using known techniques. Once trained, the Emotional-Imaging Composer application can be configured to predict a user emotion given a set of biosignal data, based on which predicted emotion the Emotional-Imaging Composer can compose a scene with a particular particle behavior according to user preferences.

The method 600 may further include, at block 606, capturing composing data for input into the machine learning algorithm. As a part of the composing, the Emotional-Imaging Composer may cause the GUI to present "warmup" media associated with an emotion to prompt the user to provide a particular emotion. Warm-up media associated with a particular emotion may be presented to the user in response to the user's selection of that emotion for a composition that comprises a plurality of predicted emotions, particle behaviors, and sets of biosignal data. This allows the user to preselect media (images, sounds, or videos) associated with a particular emotion, to help the user evoke and attain the correct physiological state while composing a scene.

The method 608 may further include, at block 608, recording the visual representation of the particle behavior along with capturing audio, video, or both of the user performing a prompted emotion. Further, the Emotional-Imaging Composer may dynamically adjust the particle behavior thresholds, the set points, or the profile of the user to optimize visual contrast of the particles, visual synchronization of the particle behavior and the video, or other visual parameters. The recorded information may be later played back, such as in a synchronized fashion in which video or audio of the user is played in conjunction with a particle behavior or other output.

Returning to FIG. 3 at block 306, the process 300 may involve composing and/or outputting a scene. Additional details regarding composing and/or outputting a scene are described with regard to FIG. 7.

Figure 7:
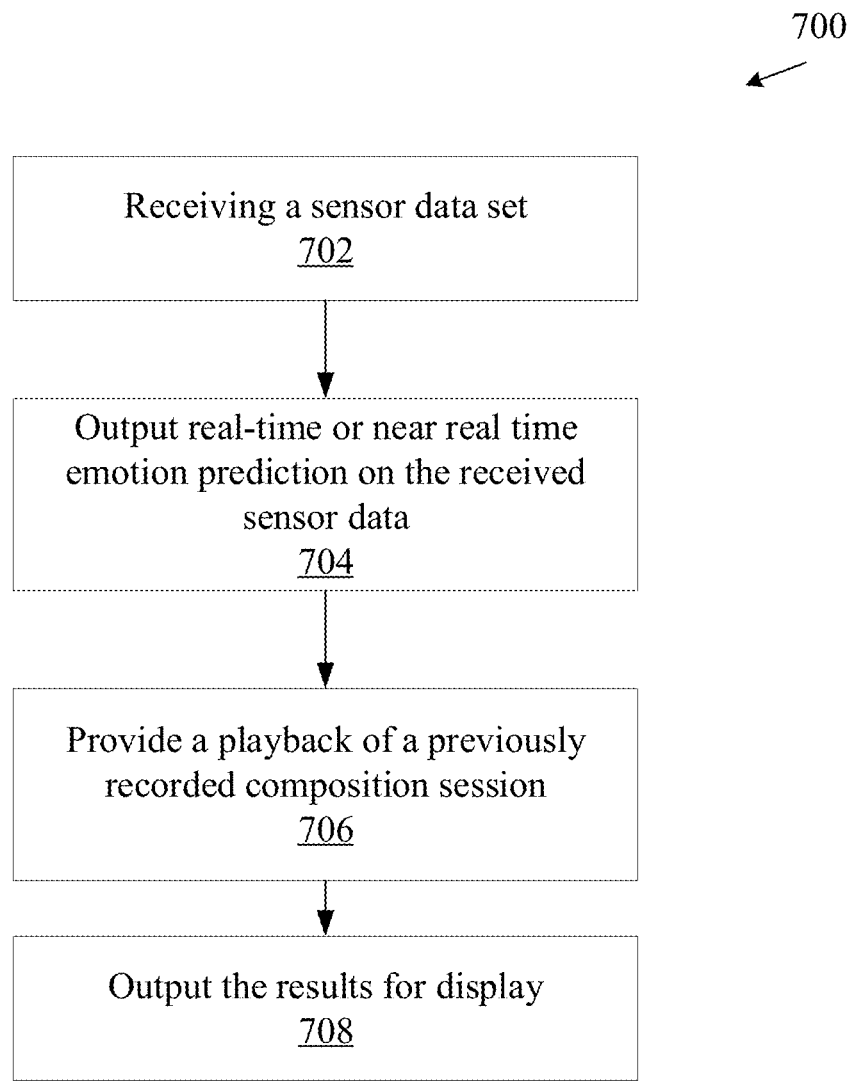
FIG. 7 depicts an example of a process flow of outputting results for the Emotional-Imaging Composer, according to embodiments of the present disclosure.

FIG. 7 is a flow chart illustrating an example method 700 of composing and outputting a scene. One or more portions of the method 700 may be performed by the emotion prediction module 130, in some embodiments. The method 700 may include, at block 702, receiving a sensor data set. The received sensor data set may be a real-time stream of data from one or more sensors, in some embodiments. Additionally or alternatively, the received sensor data set may be previously-recorded data from one or more sensors.

The method 700 may further include, at block 704, determining (that is, predicting) an emotion based on the received sensor data and generating an output based on the predicted emotion. The Emotional-Imaging Composer may compute one or more probabilities of each emotion and determine a predicted emotion (e.g., the most probable emotion). The Emotional-Imaging Composer may map the emotion state onto a 2D valence-arousal grid. In one embodiment, the coordinates of the 2D valence-arousal grid are set using definitions corresponding to the limits of valence and arousal values which correspond to the distal corners of each quadrant of the design quadrant, as shown in FIG. 4A. Block 704 may further include generating an output, such as a particle behavior, based on the determined emotion.

The method may further include, at block 706, generating a playback of a previously recorded composition session (e.g., in a "performance" mode of the Emotional-Imaging Composer composer). In the performing mode, the Emotional-Imaging Composer may generate a playback output including a particle behavior and additional content (e.g., recorded video/audio/etc.). In some embodiments, the Emotional-Imaging Composer may receive or present video/audio/etc. via the end user device or another input/output device. Further, the Emotional-Imaging Composer may provide the user a GUI to adjust the particle behavior thresholds, the set points, the profile of the user, frame rate, or other visual parameters during playback. The Emotional-Imaging Composer may save any adjustments to the particle behavior to a non-transitory memory.

The method may further include, at block 708, displaying the output generated at block 704 or 706. The output may be displayed on one or more commodity computer displays, in some embodiments, but can also be presented via one or more projectors, as part of projection mapping systems, as well as virtual reality headsets. Additionally or alternatively, the Emotional-Imaging Composer may output the results to an audio synthesis system that may be connected via headphones or speakers for listening. In yet another modality of output, the Emotional-Imaging Composer may output the results to haptic systems that may include vibrotactile or ultrasonic displays that are used to transduce digital signals into haptically perceptible effects. These are typically implemented using eccentric rotating mass motors, voice coils, or other electromechanical transducers that can convert input electrical signals into mechanical vibrations. In all these cases, the potential to stream the results for consumption remotely via the internet is possible.

Returning to FIG. 4B, FIG. 4B depicts an example of a GUI 410 for adjusting particle behavior control for Emotional-Imaging Composer, according to embodiments of the present disclosure. As described with regard to FIGS. 3-4A, the Emotional-Imaging Composer may generate a profile for a user based on user input or an automated profile generation. The Emotional-Imaging Composer may determine various particle behaviors corresponding to each emotion. In one example, the Emotional-Imaging Composer may change various aspects of particle behavior based on the emotion.

Although several embodiments have been disclosed, it should be recognized that these embodiments are not exclusive to each other, and certain elements or features from one embodiment may be used with another.

Hereinafter, general embodiments of implementation of the systems and methods of the invention will be described. As discussed above, a user interface is utilized by a processing machine that performs a set of instructions such that the processing machine processes data for a user. The user interface is typically used by the processing machine for interacting with a user either to convey information or receive information from the user. However, it should be appreciated that in accordance with some embodiments of the system and method of the invention, it is not necessary that a human user actually interact with a user interface used by the processing machine of the invention. Rather, it is also contemplated that the user interface of the invention might interact, i.e., convey and receive information, with another processing machine, rather than a human user. Accordingly, the other processing machine might be characterized as a user. Further, it is contemplated that a user interface utilized in the system and method of the invention may interact partially with another processing machine or processing machines, while also interacting partially with a human user.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications or equivalent arrangements.

What is claimed is:

1. A method for an Emotional-Imaging Composer, the method comprising:
   recording a real-time biosignal from a plurality of biosignal sensors;
   determining an emotion that is associated with the real-time biosignal;
   outputting a display feature corresponding to the emotion, wherein the display feature is a lighting effect on a graphical user interface; and
   determining a second emotion that is associated with a second real-time biosignal at a second time interval, wherein determining the second emotion comprises determining, on a design quadrant, a location of the second emotion.

2. The method of claim 1 further comprising:
   training an emotion determination model to create a trained emotion determination model, wherein the training comprises:
      prompting a user to perform a training emotion;
      receiving training biometric signals during while the user is performing the training emotion; and
      determining, on a design quadrant, a location of a reference set point associated with the training biometric signals and the training emotion.

3. The method of claim 2, wherein determining the emotion comprises comparing the reference set point with a first set point corresponding to the real-time biosignal.

4. The method of claim 2, wherein determining the emotion associated with the real-time biosignal comprises applying the trained emotion determination model to the real-time biosignal.

5. The method of claim 1, wherein the lighting effect on a graphical user interface comprises a behavior of a particle cloud.

6. The method of claim 5, wherein the behavior of the particle cloud comprises one or more of a color of each particle of the particle cloud, lifetime of each particle of the particle cloud, velocity of each particle of the particle cloud, and a maximum number of particles in the particle cloud.

7. A non-transitory, computer-readable medium storing instructions that, when executed by a processor, cause the processor to perform a method comprising:
   training an emotion determination model to create a trained emotion determination model, wherein the training comprises:

prompting a user to perform a training emotion;
receiving training biometric signals while the user is performing the training emotion; and
determining, on a design quadrant, a location of a reference set point associated with the training emotion, the training biometric signals, and the training emotion;
recording a real-time biosignal from a plurality of biosignal sensors;
determining an emotion that is associated with the real-time biosignal; and
outputting a display feature corresponding to the emotion, wherein the display feature is a lighting effect on a graphical user interface.

8. The non-transitory, computer-readable medium of claim 7, wherein determining the emotion comprises comparing the reference set point with a first set point corresponding to the real-time biosignal.

9. The non-transitory, computer-readable medium of claim 7, wherein determining the emotion associated with the real-time biosignal comprises applying the trained emotion determination model to the real-time biosignal.

10. The non-transitory, computer-readable medium of claim 7, wherein the lighting effect on a graphical user interface comprises a behavior of a particle cloud.

11. The non-transitory, computer-readable medium of claim 10, wherein the behavior of the particle cloud comprises one or more of a color of each particle of the particle cloud, lifetime of each particle of the particle cloud, velocity of each particle of the particle cloud, or a maximum number of particles in the particle cloud.

12. The non-transitory, computer-readable medium of claim 7, the instructions that, when executed by a processor, cause the processor to perform the method further comprising determining a second emotion that is associated with a second real-time biosignal at a second time interval, wherein determining the second emotion comprises determining, on a design quadrant, a location of the second emotion.

13. A system comprising:
a plurality of sensors; and
a computer-readable medium storing instructions that, when executed by a processor, cause the processor to perform a method comprising:
recording a real-time biosignal from a plurality of biosignal sensors;
determining an emotion that is associated with the real-time biosignal; and
outputting a display feature corresponding to the emotion, wherein the display feature is a lighting effect on a graphical user interface, and wherein the lighting effect comprises a behavior of a particle cloud.

14. The system of claim 13, wherein the instructions, when executed by the processor, cause the processor to perform the method further comprising:
training an emotion determination model to create a trained emotion determination model, wherein the training comprises:
prompting a user to perform a training emotion;
receiving training biometric signals during while the user is performing the training emotion; and
determining, on a design quadrant, a location of a reference set point associated with the training emotion, the training biometric signals, and the training emotion.

15. The system of claim 14, wherein determining the emotion comprises comparing the reference set point with a first set point corresponding to the real-time biosignal.

16. The system of claim 14, wherein determining the emotion associated with the real-time biosignal comprises applying the trained emotion determination model to the real-time biosignal.

17. The system of claim 13, wherein the behavior of the particle cloud comprises one or more of a color of each particle of the particle cloud, lifetime of each particle of the particle cloud, velocity of each particle of the particle cloud, or a maximum number of particles in the particle cloud.

* * * * *